United States Patent
Yang et al.

(10) Patent No.: US 7,972,645 B2
(45) Date of Patent: Jul. 5, 2011

(54) DIOSCOREA EXTRACTS FOR ENHANCING IMMUNE SYSTEM

(75) Inventors: Ning-Sun Yang, Taipei (TW); Jeng-Hwan Wang, Taipei (TW); Wen-Chi Wei, Taipei (TW)

(73) Assignee: Academia Sinica, Taipei (TW)

(*) Notice: Subject to any disclaimer, the term of this patent is extended or adjusted under 35 U.S.C. 154(b) by 66 days.

(21) Appl. No.: 12/202,528

(22) Filed: Sep. 2, 2008

(65) Prior Publication Data

US 2009/0041803 A1 Feb. 12, 2009

Related U.S. Application Data

(60) Continuation-in-part of application No. 11/331,401, filed on Jan. 12, 2006, now Pat. No. 7,419,690, which is a division of application No. 10/725,823, filed on Dec. 1, 2003, now abandoned.

(51) Int. Cl.
*A61K 36/8945* (2006.01)
*A61K 36/00* (2006.01)

(52) U.S. Cl. .................. 426/637; 424/725

(58) Field of Classification Search .................. None
See application file for complete search history.

(56) References Cited

U.S. PATENT DOCUMENTS

| | | | | |
|---|---|---|---|---|
| 6,372,227 | B1 * | 4/2002 | Garcon et al. | 424/283.1 |
| 2005/0118292 | A1 * | 6/2005 | Yang et al. | 424/773 |
| 2006/0068036 | A1 * | 3/2006 | Wu | 424/725 |

FOREIGN PATENT DOCUMENTS

JP 61106516 5/1986

OTHER PUBLICATIONS

Su et al. Effect of Chinese Herbal Plant Extracts on Growth . . . FASEB Journal (Mar. 7, 2001) vol. 15, No. 4, pp. A673. print, Annual Meeting of the Federation of American Societies for Experimental Biology on Experimental Biology 2001. Orlando, Florida, USA, Mar. 31-Apr. 4, 2001.*
Michael A. Ang-Lee et al. "Herbal Medicines and Perioperative Care". JAMA 286(2):208-216, Jul. 11, 2001.
Mohsen Araghiniknam et al. "Antioxidant Activity of Dioscorea and Dehydroepiandrosterone (DHEA) in Older Humans". Life Sciences 59(11):147-157, 1996.
Joseph Bolen et al. "Leukocyte Protein Tyrosine Kinases: Potential Targets for Drug Discovery". Annu. Rev. Immunol. 15:371-404, 1997.
Andrea Borchers et al. "Inflammation and Native American medicine: the role of botanicals". Am J Clin Nutr 72:339-347, 2000.
Donald P. Briskin et al. "Medicinal Plants and Phytomedicines. Linking Plant Biochemistry and Physiology to Human Health". Plant Physiology 124:507-514, Oct. 2000.
Xuetao Cao et al. "Augmentation of Hematopoiesis by Fibroblast-Mediated Interleukin-6 Gene Therapy in Mice with Chemotherapy". Journal of Interferon and Cytokine Research 18:227-233, 1998.

(Continued)

*Primary Examiner* — Patricia Leith
(74) *Attorney, Agent, or Firm* — Occhiuti Rohlicek & Tsao LLP

(57) ABSTRACT

An extract from a tuber of a *Dioscorea* plant is disclosed. Also disclosed is a composition containing an extract from a tuber of a *Dioscorea* plant, as well as methods of using the extract and composition.

8 Claims, 3 Drawing Sheets

OTHER PUBLICATIONS

Longwen Chen et al. "Oxidative DNA Damage in Prostrate Cancer Patients Consuming Tomato Sauce-Based Entrees as a Whole-Food Intervention". Journal of National Cancer Institute 93(24):1872-1879, Dec. 19, 2001.

N. L. Currier et al. "Deleterious effects of Echinacea purpurea and melatonin on myeloid cells in mouse spleen and bone marrow". Journal of Leukocyte Biology 70:274-276, Aug. 2001.

Jared Gollob et al. "The Functional Synergy Between IL-12 and IL-2 Involves p38 Mitogen-Activated Protein Kinase and Is Associated with the Augmentation of STAT Serine Phosphorylation". The Journal of Immunology 162:4472-4481, 1999.

Larry Karnitz et al. "Interleukin-2 Triggers a Novel Phosphatidylinositol 3-Kinase-Dependent MEK Activation Pathway". Molecular and Cellular Biology 15(6):3049-3057, Jun. 1995.

Jonathan Kelmanson et al. "Zulu medicinal plants with antibacterial activity". Journal of Ethnopharmacology 69:241-246, 2000.

Warren Leonard et al. "JAKS and STATS: Biological Implications". Annu. Rev. Immunol. 16:293-322, 1998.

Manas Majumdar et al. "Isolation, Characterization, and Chondrogenic Potential of Human Bone Marrow-Derived Multipotential Stromal Cells". Journal of Cellular Physiology 185:98-106, 2000.

Sean Morrison et al. "The Long-Term Repopulation Subset of Hematopoietic Stem Cells Is Deterministic and Isolatable by Phenotype". Immunity 1:661-673, Nov. 1994.

Frank Ruschitzka et al. "Acute heart transplant rejection due to Saint John's wort". The Lancet 355:548-549, Feb. 12, 2000.

James Crawley et al. "T Cell Proliferation in Response to Interleukins 2 and 7 Requires p38MAP Kinase Activation". The Journal of Biological Chemistry 272(23):15023-15027, 1997.

Troy Randall et al. "Phenotypic and Functional Changes Induced at the Clonal Level in Hematopoietic Stem Cells After 5-Fluorouracil Treatment". Blood 89(10):3596-3606, 1997.

Gerald Spangrude et al. "Purification and Characterization of Mouse Hematopoietic Stem Cells". Science 241:58-62, Jul. 1, 1988.

David Vistica et al. "Tetrazolium-based Assays for Cellular Viability: A Critical Examination of Selected Parameters Affecting Formazan Production". Cancer Research 51:2515-2520, May 15, 1991.

Yu Wang, MD et al. "Phytochemicals potentiate interleukin-2 generated lymphokine-activated killer cell cytotoxicity against murine renal cell carcinoma". Mol. Biother. 4:143-146, Sep. 1992.

Pawel Wlodarski et al. "Role of p53 in Hematopoietic Recovery After Cytotoxic Treatment". Blood 91(8):2998-3006, Apr. 15, 1998.

Z.-Q. Ye et al. "Establishment of an adherent cell feeder layer from human umbilical cord blood for support of long-term hematopoietic progenitor cell growth". Proc. Natl. Acad. Sci. USA 91:12140-12144, Dec. 1994.

Robert Yuan et al. "Traditional Chinese medicine: an approach to scientific proof and clinical validation". Pharmacology & Therapeutics 86:191-198, 2000.

Carias, M. "Sanococho with Seven Meats," Feb. 17, 2002 URL <http://www.allbaking,net/mf/3/6027> 3 pages.

Su et al. "Effect of Chinese Herbal Plant Extracts on Growth . . . ," FASEB Journal (Mar. 7, 2001) vol. 15, No. 4, pp. A673 Experimental Biology on Experimental Biology 2001, Orlando, Florida USA, Mar. 31-Apr. 4, 2001.

Stephens, J. Yams-Dioscorea spp., University of Florida IFAS Extension, URL ,www.http://edis.ifas.ufl.edu/MV153, printed on Apr. 24, 2006.

* cited by examiner

DIOSCOREA EXTRACTS FOR ENHANCING IMMUNE SYSTEM

RELATED APPLICATION

This application is a continuation-in-part application of, and claims priority to, U.S. application Ser. No. 11/331,401, filed on Jan. 12, 2006 and now allowed, which is a divisional application, and claims priority to, U.S. application Ser. No. 10/725,823, filed on Dec. 1, 2003. The contents of both applications are incorporated herein in their entirety.

BACKGROUND

The immune system defends the human body against pathogen infection, cellular transformation, and physical/chemical damage. Its impairment, such as decrease in the number of spleen- or bone marrow-derived immune cells, leads to various disorders. The impairment can be caused by aging, disease, and medical treatment (e.g., chemotherapy or immunosuppression). There is a need for drugs that improve the immune system.

SUMMARY

This invention is based, at least in part, on unexpected discoveries that an extract prepared from a tuber of a *Dioscorea* plant increased the activities of a NF-κB-inducible ELAM-1 composite promoter and a GM-CSF promoter and protected animals against certain cancer. This extract thus can be used to improve the immune system for treating pathogen infection and cellular transformation, and for recovery from physical/chemical damage.

One aspect of the invention features an extract from a tuber of a *Dioscorea* plant, which is soluble in water and insoluble in an aqueous solution containing 65-90% ethanol, such as 70-80% (e.g., 75%) ethanol, between 0° C. and 25° C. The extract can be prepared from *D. batatas* Decne, *D. alata* L., *D. pseudojaponica*, or *D. alata* L. var. *purpurea* (Roxb.) M. Pouch. In a preferred embodiment, it is prepared from *D. batatas* Decne.

The invention also features an immunogenic composition that contains an antigen agent and an adjuvant agent, wherein the adjuvant agent contains an extract that is prepared from a tuber of a *Dioscorea* plant. In a preferred embodiment, the extract is a DsCE-I extract prepared by a process including: (a) obtaining an aqueous extract of a tuber of *Dioscorea* plant; (b) extracting the extract of part (a) with an aqueous solution containing 50% ethanol to form a first supernatant and a first ethanol-insoluble fraction; and (c) collecting the first ethanol-insoluble fraction. The first ethanol-insoluble fraction is DsCE-I, and the *Dioscorea* plant can be *D. batatas* Decne, *D. alata* L., *D. pseudojaponica*, or *D. alata* L. var. *purpurea* (Roxb.) M. Pouch. The antigen agent can be a polypeptide, such as a viral protein or a tumor antigen protein or a nucleic acid encoding the polypeptide.

In another aspect, the invention features a method of generating an immune response in a subject. The method includes administrating to a subject in need thereof the above-mentioned composition. The invention also features a method for improving an immune response to an immunogenic antigen in a subject. The method includes administering to a subject in need thereof a composition containing an immunogenic antigen; and further administering to the subject an adjuvant agent contains an extract that is prepared from a tuber of a *Dioscorea* plant, such as the just-mentioned DsCE-I extract.

In yet another aspect, the invention features a method for increasing the expression level of GM-CSF in a cell. The method includes contacting a cell having a nucleic acid encoding GM-CSF a DsCE-I extract prepared from a *Dioscorea* plant. The nucleic acid is operably linked to an hGM-CSF promoter. Within the scope of the invention is a method for enhancing the level of granulocytes or monocytes in a subject. The method includes administering to a subject in need thereof a composition containing an effective amount of the above-mentioned DsCE-I extract.

In a further aspect, the invention features a method for treating a cellular proliferative disorder in a subject, e.g., a human patient or an animal. The method includes administering to a subject in need thereof an effective amount of an immunogenic composition containing an antigen agent, and further administering to the subject an adjuvant agent contains an extract that is prepared from a tuber of a *Dioscorea* plant. The antigen agent contains a polypeptide that contains a polypeptide sequence of a viral protein or a tumor antigen protein or a nucleic acid having a sequence encoding the polypeptide. A cellular proliferative disorder refers to a disorder characterized by uncontrolled, autonomous cell growth, including malignant and non-malignant growth. An example is melanoma and a related tumor antigen protein is gp 100 melanoma antigen.

The details of one or more embodiments of the invention are set forth in the accompanying description below. Other features, objects, and advantages of the invention will be apparent from the description, figures, and from the claims.

DETAILED DESCRIPTION

Figure 1:
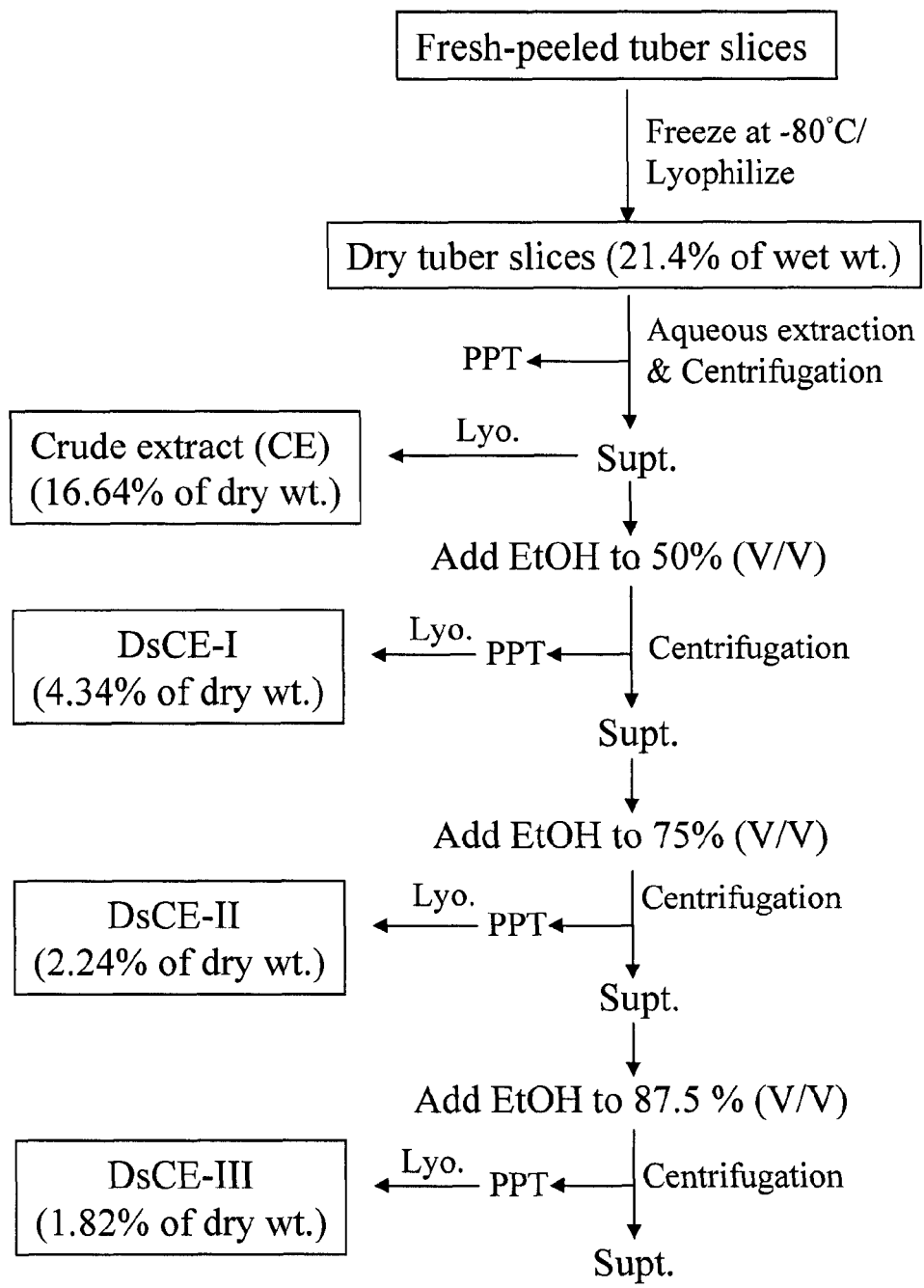
FIG. 1 is schematic representation of a process of making the extracts described in this application.

This invention relates to an extract prepared from *Dioscorea* and its use in enhancing the proliferation of certain bone marrow cells and spleen cells, in improving the immune system, and in immuno-therapy against infection and cancer.

For example, within the scope of this invention is an extract prepared from a tuber of a *Dioscorea* plant. This extract can be prepared according to the procedure shown in FIG. 1 and descried in the example below. It is soluble in water and insoluble in an aqueous solution containing 65-90% ethanol between 0° C. and 25° C. Many species of the genus *Dioscorea*, such as *D. batatas* Decne, *D. alata*, L., and *D. pseudojaponica* can be used. Their cultivation, growth, taxonomy, and agricultural practice are well known in the art. See, e.g., Liu et al. 1995, J. Chinese Med. 6:111-126.

It was unexpected that one of the extracts, DsCE-I, not only increases the activities of a NF-κB-inducible ELAM-1 composite promoter and a GM-CSF promoter, but also protects animals against certain cancer. NF-κB is a protein complex functioning as a transcription factor. It plays a key role in regulating the immune response to infection. Consistent with this role, incorrect regulation of NF-κB has been linked to cancer, inflammatory, and autoimmune diseases, septic shock, viral infection, and improper immune development. NF-κB has also been implicated in processes of synaptic plasticity and memory. GM-CSF is a cytokine that functions as a white blood cell growth factor. GM-CSF stimulates stem cells to produce granulocytes (neutrophils, eosinophils, and basophils) and monocytes. Monocytes exit the circulation and migrate into tissue, whereupon they mature into macrophages. GM-CSF is thus part of the immune/inflammatory cascade, by which activation of a small number of macrophages can rapidly lead to an increase in their numbers, a process crucial for fighting infection. The active form of the protein is found extracellularly as a homodimer.

Since DsCE-I increases the activities of a NF-κB-inducible ELAM-1 composite promoter and a GM-CSF promoter, DsCE-I can be used to enhance the production of the above-mentioned immune cells and thereby improve the body's immune system. The extract can be used alone or in combination with other compound, such as cytokines (e.g., TNF-α, IL-8, IL-12, IL-2 and IL-6), to enhance the proliferation of the cells. In particular, it can be used as an adjuvant agent or adjuvant. As used herein, the term "adjuvant agent" or "adjuvant" means a substance added to an immunogenic composition or a vaccine to increase the immunogenic composition or the vaccine's immunogenicity.

The adjuvant of the invention can be used to enhance the immune response to an antigen of a vaccine formulation. The adjuvant of the invention can be used with antigens derived from any bacteria or from any virus, provided the antigen does not get destroyed or denatured. The adjuvant is also useful in vaccine compositions that contain an antigen as described in U.S. Pat. Nos. 5,616,328 and 5,084,269. It may be useful in conjunction with any material that raises either humoral and/or cell mediated immune response, such as, for example, live viral, bacterial, or parasitic antigens; inactivated viral, tumor-derived, protozoal, organism-derived, fungal, or bacterial antigens, toxoids, toxins; self-antigens; polysaccharides; proteins; glycoproteins; peptides; cellular vaccines; DNA vaccines; recombinant proteins; glycoproteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease. Especially, materials such as recombinant proteins, glycoproteins, and peptides that do not raise a strong immune response can be used in connection with the adjuvant of the invention.

In certain embodiments, the antigen may be a cancer antigen or a tumor antigen. The terms cancer antigen and tumor antigen are used interchangeably and refer to an antigen that is differentially expressed by cancer cells. Therefore, cancer antigens can be exploited to differentially target an immune response against cancer cells. Cancer antigens may thus potentially stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-C017-1A/GA733, Carcinoembryonic Antigen (CEA) and its antigenic epitopes CAP-1 and CAP-2, etv6, aml1, Prostate Specific Antigen (PSA) and its antigenic epitopes PSA-1, PSA-2, and PSA-3, prostate-specific membrane antigen (PSMA), T-cell receptor/CD3-.zeta. chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, aml1, cyclophilin b), B cell lymphoma (Ig-idiotype), glioma (E-cadherin, α-catenin, β-catenin, γ.-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

The adjuvant of the invention may be used in a vaccine formulation to immunize an animal. Thus, within the scope of this invention is an immunogenic or vaccine composition containing an antigenic agent and an adjuvant agent. The adjuvant agent contains the DsCE-I extract and, once administered to a subject, enhances the subject's immune response to the antigenic agent. The term "immunogenic" refers to a capability of producing an immune response in a host animal against an antigen or antigens. This immune response forms the basis of the protective immunity elicited by a vaccine against a specific infectious organism. "Immune response" refers to a response elicited in an animal, which may refer to cellular immunity (CMI); humoral immunity or both. "Antigenic agent," "antigen," or "immunogen" means a substance that induces a specific immune response in a host animal. The antigen may contain a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin. The term "animal" includes all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cattle), porcine (e.g., pigs), as well as in avians. The term "avian" as used herein refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary.

In one embodiment, the vaccine formulation contains the adjuvant of the invention and an antigen. The optimal ratios of each component in the vaccine formulation may be determined by techniques well known to those skilled in the art.

A vaccine formulation may be administered to a subject per se or in the form of a pharmaceutical or therapeutic composition. Pharmaceutical compositions comprising the adjuvant of the invention and an antigen may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen. For purposes of this application, "physiologically acceptable carrier" encompasses carriers that are acceptable for human or animal use without relatively harmful side effects (relative to the condition being treated), as well as diluents, excipients or auxiliaries that are likewise acceptable. Systemic formulations include those designed for administration by injection, e.g. subcutaneous, intradermal, intramuscular or intraperitoneal injection.

For injection, the vaccine preparations may be formulated in aqueous solutions, preferably in physiologically compatible buffers such as Hanks's solution, Ringer's solution, phosphate buffered saline, or any other physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 µg. Suitable dose range will vary with the route of injection and the size of the patient, but will typically range from about 0.1 mL to about 5 mL.

Also within the scope of this invention is a composition containing the above-described extract or a cytokine as an active ingredient. Additional ingredients that can be contained in the composition include other herbal extracts, vitamins, amino acids, metal salts, metal chelates, coloring agents, flavor enhancers, preservatives, and the like.

An extract or composition of this invention can be added directly to foods so that an effective amount of the extract is ingested during normal meals. Any methods known to those skilled in the art can be used to add to or incorporate the compositions of this invention into natural or processed foods, provided that the extract remains effective. For example, the composition of the invention can be made and stored at a temperature from about 0° C. to 4° C. "Food" broadly refers to any kind of material, liquid or solid that is used for nourishing an animal, and for sustaining normal or accelerated growth of an animal including humans. Many types of food products or beverages, such as, but not limited to, fruit juice, herbal extracts, tea-based beverages, dairy products, soy bean product (e.g., tofu), and rice products, can be used to form compositions containing the extract of the invention.

A composition of this invention can be a pharmaceutical composition that contains a pharmaceutically acceptable carrier, such as a solvent, a dispersion medium, a coating, an antibacterial and antifungal agent, and an isotonic and absorption delaying agent. The composition can additionally include binding agents (e.g., pregelatinized maize starch, polyvinylpyrrolidone, or hydroxypropyl methylcellulose); binders or fillers (e.g., lactose, pentosan, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets or capsules can be coated by methods well known in the art.

An above-described composition can be formulated to be compatible with its intended route of administration, e.g., oral administration. Such a composition can be formulated as discrete units such as capsules, cachets, or tablets, each containing a predetermined amount of the extract, as a powder or granules or as a solution or a suspension in an aqueous liquid, a non-aqueous liquid, an oil-in-water emulsion, or a water-in-oil liquid emulsion. In general, the compositions are prepared by uniformly and intimately admixing the extract with liquid carriers or finely divided solid carriers or both, and then, if necessary, shaping the product into the desired presentation. Liquid preparations for oral administration can take the form of, for example, solutions, syrups, or suspensions; or they can be presented as a dry product for constitution with water or other suitable vehicle before use. For instance, the extract described above can be directly packed into vacuum-sealed bottles for use as liquid compositions. The temperature of the liquid used to reconstitute the dried product should be less than 65° C. The liquid preparations can also be prepared by conventional means with additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates, or sorbic acid). Alternatively, as described below, the preparations can be made to resemble foods, containing buffer salts, flavoring, coloring and sweetening agents as appropriate.

The above-described extract or composition can be used as a medicament for treatment of immune system impairment. It may also be particularly helpful in individuals having compromised immune function. For example, the extract or composition may be used for treating the opportunistic infections and tumors that occur after suppression of cell mediated immunity in, for example, transplant patients, cancer patients and HIV patients.

It also can be used as a dietary supplement, health food, or health drink for prevention of immune system impairment. Subjects to be treated can be identified as having, or being at risk for acquiring, a condition characterized by immune system impairment, e.g., low level of spleen- or bone marrow-derived cells.

For example, patients undergoing chemotherapies or immune-suppressing therapies have low level of immune cells and often suffer from disorders associated with immune system impairment. To restore the immune cell level after the therapies, the patients can be treated with the extract or composition of this invention. In an ex vivo approach, the composition is administered to tissues (e.g., blood and bone marrow) or cells (e.g., tumor infiltrating lymphocytes or lymphokine-activated killer cells) obtained from a subject. The tissues or cells are then introduced back into the subject. In an in vivo approach, a composition of the invention is administered orally or by intravenous infusion, or injected or implanted subcutaneously, intramuscularly, intrathecally, intraperitoneally, intrarectally, intravaginally, intranasally, intragastrically, intratracheally, or intrapulmonarily. This treatment can be performed alone or in conjunction with other drugs or therapy.

The composition of the invention can also be used to therapeutically treat a condition treatable by a cell-mediated immune response. Such a therapeutic composition can be provided in further combination with one or more pharmaceutically acceptable carriers. Each component may be administered in any suitable conventional dosage form such as, for example, tablets, lozenges, parenteral formulations, syrups, creams, ointments, aerosol formulations, transdermal patches, transmucosal patches and the like. The composition can be administered as the single therapeutic agent in a treatment regimen. Alternatively, it can be administered in combination with another therapeutic composition, or with other active agents such as antivirals, antibiotics, etc. Because of its effect on while blood cells, the composition of this invention can be particularly useful for treating viral diseases and tumors. This immunomodulating activity suggests that the immunogenic or vaccine composition of the invention is useful in treating conditions such as, but not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection; and (d) neoplastic diseases, such as, for example, intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers (e.g., cancers identified above).

Thus, the invention also provides a method of treating a viral infection in an animal and a method of treating a neoplastic disease in an animal comprising administering a therapeutically effective amount of the immunogenic composition of the invention to the animal. Administration refers to intake of the extract or composition in any suitable form (e.g., pharmaceutical compositions, food product, beverage, and tablet). An effective amount refers to an amount of the above-described extract or composition that is sufficient to provide a therapeutic or healthful benefit, i.e., enhancing the proliferation of bone marrow or spleen cells (e.g., while blood cells) or reducing the probability of relapse after a successful course of treatment. A therapeutically effective amount to treat or inhibit a viral infection is an amount that will cause a reduction in one or more of the manifestations of viral infection, such as viral lesions, viral load, rate of virus production, and mortality as compared to untreated control animals. A therapeutically effective amount of a combination to treat a neoplastic condition is an amount that will cause, for example, a reduction in tumor size, a reduction in the number of tumor foci, or slow the growth of a tumor, as compared to untreated animals.

Figure 2A:
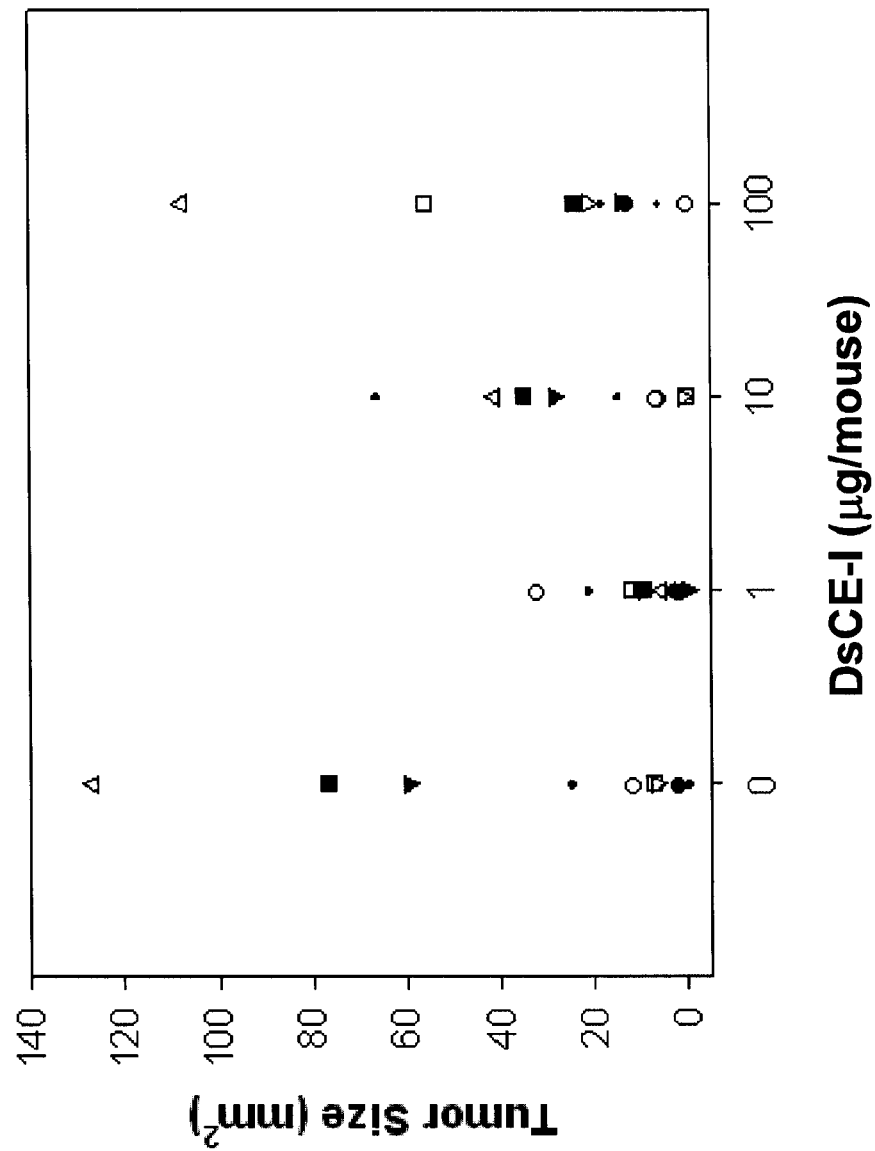
FIGS. 2A and 2B are two diagrams showing that a DsCE-I extract enhanced the efficacy of a gp 100 DNA vaccine against melanoma in mice.
Figure 2B:
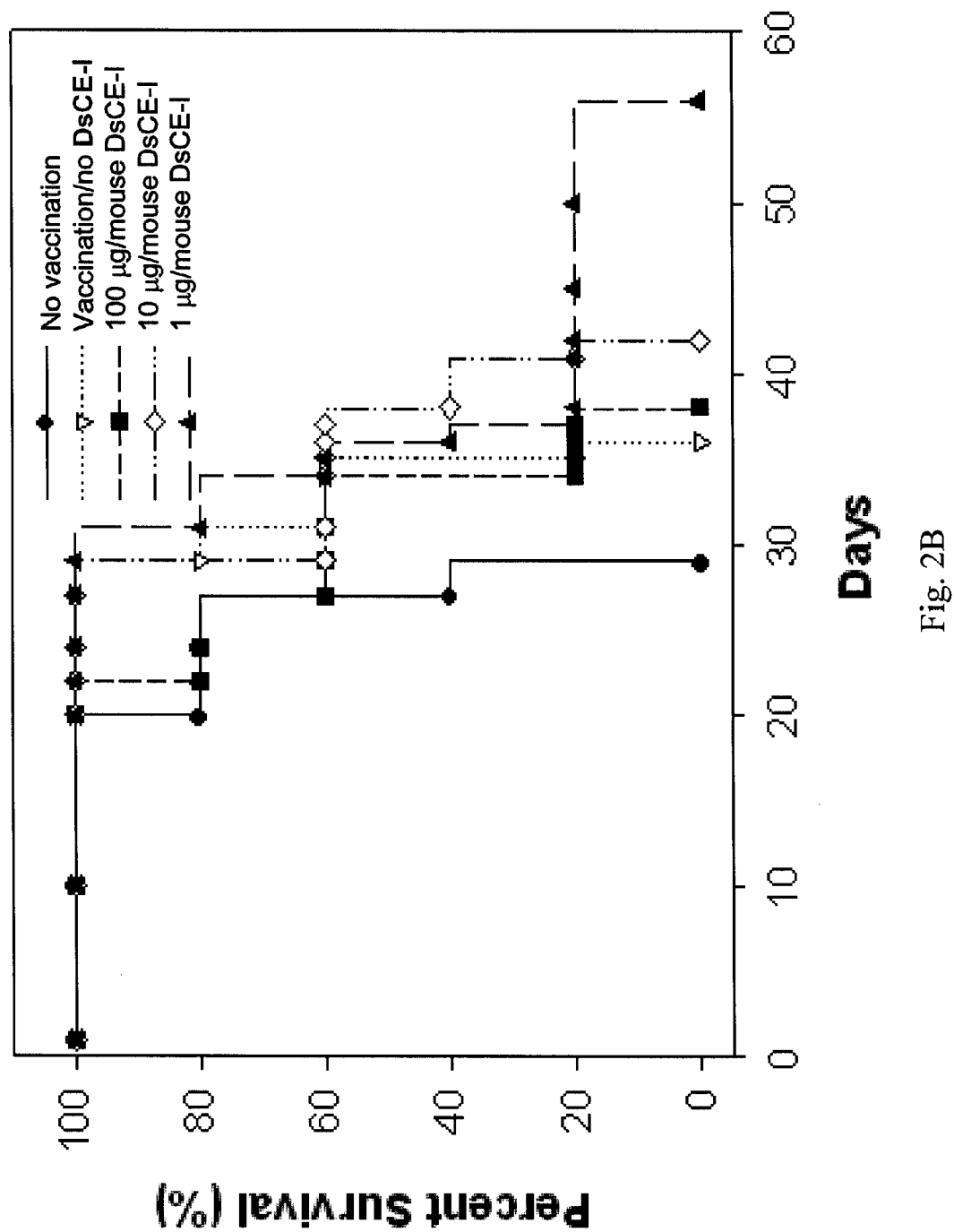

In one particular embodiment, the composition of the invention may be used to inhibit tumor growth in vivo. Subjects having tumor cells expressing a particular antigen may be immunized with a therapeutic combination that contains DsCE-I and, optionally, the antigen. In some embodiments, the therapy can include an initial immunization and a second booster immunization. Tumors taken from subjects immunized with a therapeutic combination of the invention were generally smaller than the tumors harvested from either (a) non-immunized subjects, or (b) subjects immunized with only the antigen (FIGS. 2A and 2B).

The term "treating" is defined as administration of a composition to a subject with the purpose to cure, alleviate, relieve, remedy, prevent, or ameliorate a disorder, the symptom of immune system impairment, the disease state secondary to the disorder, or the predisposition toward the disorder. The efficacy of an extract or composition of this invention can be evaluated for its ability to enhance the proliferation of bone marrow cells and spleens cells in the manner described in U.S. application Ser. No. 11/331,401 or for its ability to inhibit cancer in the manner described in the example below or. Based on the results, an appropriate dosage range and administration route can be determined.

To determine optimal administration doses and routes, animal studies or clinical trials can also be conducted. The dosage required depends on the choice of the route of administration; the nature of the formulation; the nature of the subject's illness; the subject's size, weight, surface area, age, and sex; other drugs being administered; and the judgment of the attending physician. It can be adjusted by one skilled in the art, e.g., a nutritionist, dietician, or treating physician, in conjunction with the subject's response. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE 1

Preparation of *Dioscorea* Extracts

Three species of the genus *Dioscorea* (*D. batatas* Decne, *D. alata*, L. and *D. pseudojaponica*) and one cultivar of *D. alata* (*D. alata* L. var. *purpurea* (Roxb.) M. Pouch.) were used to prepare extracts. The authenticity of all *Dioscorea* plant materials was validated by Dr. Sin-Yie Liu at Taiwan Agricultural Research Institute.

The process for making extracts is shown FIG. 1. More specifically, tubers of *Dioscorea* spp. were peeled, sliced (2-4 mm), frozen at −80° C., lyophilized, and stored in a desiccator at room temperature until use. The tuber slices were ground to powder. Ten grams of the powder was mixed with 100 ml milli Q water, stirred for 1 hour (h) at room temperature, and centrifuged at 24,000×g at 4° C. for 20 min. The resultant supernatant ("Supt") was filtered through glass wool to further get rid of non-dissolvable substances. The precipitate ("PPT") or non-dissolvable pellet collected from the centrifugation was resuspended in 100 ml water, stirred, centrifuged, and re-extracted in the manner described above. The supernatants from the two extractions were pooled to generate a crude extract (CE) fraction in form of an aqueous solution. The CE fraction was either lyophilized to generate dried form CE or was further processed stepwise with addition of ethanol so that the original CE aqueous solution contains 50%, 75%, and 87.5% (V/V) of ethanol with the balance being water to generate extracts DsCE-II, -II, and -III, respectively. In particular, the extract DsCE-I was generated in from of a precipitate by adding ethanol to the CE aqueous solution that was obtained with the procedure discussed above to an extent that ethanol content reached about 50% (V/V) of the liquid phase. The precipitate or pellet was separated from the supernatant and collected by centrifugation at 24,000×g at 4° C. for 20 min. The extract DsCE-II was obtained in a following step in form of a precipitate by further adding ethanol to the supernatant from the previous step till the ethanol content reached about 75% (V/V) of the liquid phase. The DsCE-II precipitate or pellet was separated from the supernatant and collected by centrifugation at 24,000×g at 4° C. for 20 min. The extract DsCE-III was then obtained in a final step in form of a precipitate by further adding ethanol to the supernatant from the previous step till the ethanol content reached about 87.5% (V/V) of the liquid phase. The DsCE-III precipitate or pellet was separated from the supernatant and collected by centrifugation at 24,000×g at 4° C. for 20 min. In each step, loss of water and/or ethanol in liquid phase, e.g., during centrifugation and separation from the respective precipitate, was negligible, and the DsCE-I, -II, and -III pellets were lyophilized for yield calculations. The yields of CE, DsCE-I, -II, and -III were 16.64%, 4.34%, 2.24%, and 1.82% of the dry weight of the starting material. The lyophilized DsCE-I, -II, and -III pellets can be dissolved in sterilized water until use to make an aqueous solution at a concentration of 10 mg/ml, respectively.

EXAMPLE 2

Effect of DsCE-I on Transgenic NF-κB-Inducible ELAM-1 Composite Promoter

NF-κB plays a key role in regulating the immune response. To investigate DsCE-I's role in the immune response, the effects of DsCE-I on transgenic NF-κB-inducible ELAM-1 composite promoter were examined.

Briefly, B16 melanoma cells were transfected with a vector carrying the human secreted embryonic alkaline phosphatase (SEAP) gene, whose expression is under the control of a NF-κB-inducible ELAM-1 composite promoter, using a standard method for reporter (SEAP) assay. B16 melanoma cells were transfected with the NF-kB-inducible reporter plasmid pNiFty-SEAP (InvivoGen) in the presence of lipofectin (Invitrogen) for 24 hours. The SEAP secreted into medium was measured according to the manufacturer's instructions (Phospha-Light™ System, Applied Biosystems).

The transfected cells were then incubated with DsCE-I before the chemiluminescent reporter gene assays were conducted. It was known that LPS increased the activity of NF-κB and p38MAPK was involved in the LPS-induced activation. Therefore, LPS (0.1 µg/ml) was used as a positive control (Group A) and the corresponding luciferase was normalized as 100%. To illustrate the specificity, the effects of inhibitors of the LPS-induced activation were also examined. These inhibitors included SB203580 ("SB," a p38MAPK inhibitor), PDTC ("PD," a NF-κB inhibitor), and Polymyxin B ("PB," an LPS-binding antibiotic). The solvent used to prepare the reagents was used as a negative control (Group J). The results are summarized in Table 1 below.

TABLE 1

DsCE-I's effects on activity of NF-κB-inducible ELAM-1 transgenic composite promoter

| | Reagents | | | | | |
|---|---|---|---|---|---|---|
| Groups | LPS (µg/ml) | DsCE-I (µg/ml) | SB (µM) | PD (µM) | PB (U) | Relative Luciferase Activity |
| A | 0.1 | | | | | 100 ± 0.62% |
| B | 0.1 | | 15 | | | 8.5 ± 0.5% |

TABLE 1-continued

DsCE-I's effects on activity of NF-κB-inducible
ELAM-1 transgenic composite promoter

| | Reagents | | | | |
|---|---|---|---|---|---|
| Groups | LPS (μg/ml) | DsCE-I (μg/ml) | SB (μM) | PD (μM) | PB (U) | Relative Luciferase Activity |
| C | 0.1 | | | 30 | | 3.7 ± 0.3% |
| D | 0.1 | | | | 400 | 0.4 ± 0.2% |
| E | | 100 | | | | 14.4 ± 0.7% |
| F | | 100 | 15 | | | 10 ± 0.97% |
| G | | 100 | | 30 | | 9% |
| H | | 100 | 15 | 30 | | 2.5 ± 0.1% |
| I | | 100 | | | 400 | 8 ± 0.4% |
| J | | | | | | 0.1 ± 0.2% |

The results suggest that DsCE-I can stimulate the transgenic composite promoter activity of NF-κB-inducible ELAM-1 in B-16 cells and therefore may modulate inflammatory immune response, e.g., for use as a cancer or viral vaccine adjuvant. The results also indicate that DsCE-I act via the TLR4, p38 and NF-κB cascade signaling pathway. Furthermore, Polymyxin B inhibited LPS-induced activation completely, but only partially inhibited DsCE-I-induced activation, suggesting that DsCE-I and LPS conferred different mode of action on NF-κB activation. Thus, DsCE- may be used as a new class of factor for immune activation and as a new tool for studying signal pathways in the immune response.

EXAMPLE 3

Effects of DsCE-I on hGM-CSF

Human GM-CSF is a cytokine that functions as a white blood cell growth factor. DsCE-I's effects on hGM-CSF's expression level was evaluated by examining its effect on an hGM-CSF promoter.

The pGM620 expression plasmid was transfected into skin tissues of BALB/c mice. One hour later, the DsCE-I extract and a number of other plant extracts were applied onto the tissues at a dosage of 10 μg/10 μl/tissue site. These other plant extracts included *Bidens pilosa* hot water extract ("*Bidens pilosa*"), *Echinacea* 70% ethanolic extract ("*Echinacea*"), sliced *Colocasia* plant tissue ("*Colocasia*"), *Dioscorea* 70% ethanolic extract ("*Dioscorea* (EtOH)"), DsCE-II, and *Dioscorea* hot water extract ("*Dioscorea* (water)"). The skin tissues were subsequently harvested for assay of transgenic luciferase activity and protein levels at 8 hour post-treatment. Water (10 μl/site) was used as a negative control. The backbone vector of pGM620, pGL-3p, was also used as a background control. The results are summarized in Table 2 below, where the data represent the results from triplicate assays.

TABLE 2

Effect of DsCE-I on hGM-CSF promoter in normal skin tissue

| Reagents | Vector | Luciferase Protein Level (pg/site) |
|---|---|---|
| Water | pGL-3 | 18.1 ± 3.2 |
| Water | pGM620 | 133 ± 27.3 |
| Bidens pilosa | pGM620 | 142 ± 18 |
| Echinacea | pGM620 | 170.4 ± 29 |
| Colocasia | pGM620 | 157.5 ± 38.3 |
| aDioscorea (EtOH) | pGM620 | 106 ± 1.2 |
| DsCE-I | pGM620 | 239.7 ± 19.2 |

TABLE 2-continued

Effect of DsCE-I on hGM-CSF promoter in normal skin tissue

| Reagents | Vector | Luciferase Protein Level (pg/site) |
|---|---|---|
| DsCE-II | pGM620 | 125 ± 15.7 |
| Dioscorea (water) | pGM620 | 123.3 ± 1.7 |

As shown in Table 2, DsCE-I enhanced the transgenic promoter activity of hGM-CSF in normal skin tissue. Therefore, this in vivo effect is consistent with the in vitro results shown in Table 1, suggesting that DsCE-I can improve the immune system via GM-CSF.

EXAMPLE 4

DsCE-I Protected Mice From B16-gp100 Melanoma

Effects of DsCE-I on protection against B16-gp100 melanoma was conducted in C57BL/6 mice. Specifically, the skin of each mouse was transfected at two sites with gp100 cDNA (2.5 μg/mouse) using gene gun. The cDNA encodes a tumor associated antigen. Seven days later (Day 0), the vaccinated mice were challenged i.d. with $5\times10^4$ B16-gp100 cells and were administered subcutaneously DsCE-I of different dosages: 1 μg/mouse, 10 μg/mouse, and 100 μg/mouse. At Day 15, the sizes of tumor at each site was measured using a standard method and the results are shown in FIG. 2A. As shown in FIG. 2A, the mice that received DsCE-I had smaller tumor diameters. The survival curves of the mice were also obtained (FIG. 2B). As shown in FIG. 2B, DsCE-I prolonged the survival time and increased the survival rate of the mice in a dose-dependent manner.

The results demonstrate that DsCE-I enhanced the efficacy of the gp100 DNA vaccine against melanoma. Therefore, DsCE-I can be used clinically as an adjuvant for vaccination against cancers or other infectious diseases.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An immunogenic composition comprising an antigen agent and an adjuvant agent, wherein the adjuvant agent contains a DsCE-I extract that is prepared from a tuber of a *Dioscorea* plant by a process including:
    (a) obtaining an aqueous extract of a tuber of *Dioscorea* plant;
    (b) extracting the extract of part (a) with an aqueous solution containing 50% ethanol to form a first supernatant and a first ethanol-insoluble fraction; and
    (c) collecting the first ethanol-insoluble fraction, wherein the first ethanol-insoluble fraction is DsCE-I, and wherein the *Dioscorea* plant is *D. batatas* Decne, *D. alata* L., *D. pseudojaponica*, or *D. alata* L. var. *purpurea* (Roxb.) M. Pouch.

2. The immunogenic composition of claim 1, wherein the antigen agent contains a polypeptide or a nucleic acid having a sequence encoding the polypeptide.

3. The immunogenic composition of claim 2, wherein the polypeptide is a viral protein or a tumor antigen protein, or an antigenic fragment thereof.

4. A method of generating an immune response in a subject, comprising administrating to a subject in need thereof the composition of claim 1.

5. A method for improving an immune response to an immunogenic antigen in a subject, comprising administering to a subject in need thereof, an effective amount of the composition of claim 1.

6. A method for enhancing the level of granulocytes or monocytes in a subject, comprising administering to a subject in need thereof, an effective amount of the composition of claim 1.

7. A method for increasing the expression level of GM-CSF in a cell, comprising contacting a cell having a nucleic acid encoding GM-CSF, an effective amount of the composition of claim 1.

8. The method of claim 7, wherein the nucleic acid is operably linked to an hGM-CSF promoter.

* * * * *